United States Patent [19]

Tomcufcik et al.

[11] 4,340,734
[45] Jul. 20, 1982

[54] 3-(α-SUBSTITUTED-BENZYL)-2,3-DIHYDROTHIAZOLO [3,2-A][1,3]DIAZACYCLAN-3-OL DERIVATIVES

[75] Inventors: Andrews S. Tomcufcik, Old Tappan; William B. Wright, Jr., Woodcliff Lake, both of N.J.; Joseph W. Marsico, Jr., Pearl River, N.Y.

[73] Assignee: American Cyanamid Company, Stamford, Conn.

[21] Appl. No.: 206,803

[22] Filed: Nov. 14, 1980

[51] Int. Cl.$^3$ .................. C07D 513/04; A61K 31/54; A61K 31/55
[52] U.S. Cl. .................. 544/282; 548/154; 260/245.5; 424/251; 424/270
[58] Field of Search .................. 544/282; 548/154

[56] References Cited

U.S. PATENT DOCUMENTS

| | | | |
|---|---|---|---|
| 2,703,329 | 3/1955 | Schultz | 260/465 |
| 3,671,534 | 6/1972 | Houlihan et al. | 548/154 |
| 3,806,515 | 4/1974 | Houlihan et al. | 548/154 |
| 3,853,872 | 12/1974 | Wei et al. | 548/154 |

OTHER PUBLICATIONS

M. J. Hatch & D. J. Cram, Jour. Amer. Chem. Soc. 75, 38 (1953).
E. J. Cragoe, Jr., Jour. Org. Chem. 23, 971 (1958).
Wagner & Zook, "Synthetic Organic Chem.", p. 428 (1953).
G. W. Wheland, "Advanced Organic Chem.", 4th Ed. (1960) pp. 462–468.

Primary Examiner—Donald G. Daus
Assistant Examiner—Sharon A. Gibson
Attorney, Agent, or Firm—Edward A. Conroy, Jr.

[57] ABSTRACT

This disclosure describes certain novel 3-(α-substituted-benzyl)-2,3-dihydrothiazolo[3,2-a][1,3]diazacyclan-3-ols which are useful as diuretic agents.

27 Claims, No Drawings

3-(α-SUBSTITUTED-BENZYL)-2,3-DIHYDRO-THIAZOLO [3,2-A][1,3]DIAZACYCLAN-3-OL DERIVATIVES

BRIEF SUMMARY OF THE INVENTION

This invention relates to new organic compounds and, more particularly, is concerned with novel 3-(α-substituted-benzyl)-2,3-dihydrothiazolo[3,2-a][1,3]diazacyclan-3-ols which may be represented by the following structural formula:

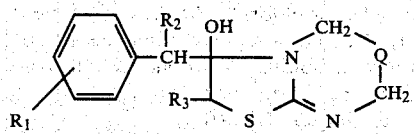

wherein Q is a divalent moiety selected from the group consisting of those of the formulae:

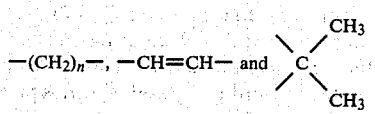

wherein n is the integer 1, 2 or 3; $R_1$ is hydrogen, fluoro, chloro, bromo, alkyl having from 1 to 3 carbon atoms or alkoxy having from 1 to 3 carbon atoms; $R_2$ is hydrogen or the moiety

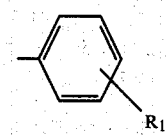

wherein $R_1$ is as hereinbefore defined; $R_3$ is hydrogen, alkyl having from 1 to 3 carbon atoms or a moiety selected from the group consisting of those of the formulae:

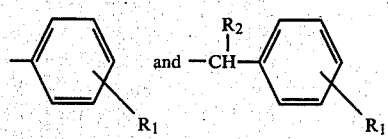

wherein $R_1$ and $R_2$ are as hereinbefore defined. The invention also includes novel compositions of matter containing the above-defined compounds useful as diuretics and the method of enhancing the excretion of sodium ions in mammals therewith.

DETAILED DESCRIPTION OF THE INVENTION

The novel compounds of the present invention are generally obtainable as white to pale yellow crystalline materials having characteristic melting points and absorption spectra and which may be purified by recrystallization from common organic solvents such as methanol, ethanol, N,N-dimethylformamide, acetone, chloroform, ethyl acetate, and the like. They are appreciably soluble in non-polar organic solvents such as toluene, carbon tetrachloride, and the like but are relatively insoluble in water. The organic bases of this invention form nontoxic acid-addition salts with a variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydriodic, sulfamic, citric, lactic, fumaric, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

The novel compounds of the present invention may be readily prepared as set forth in the following reaction scheme:

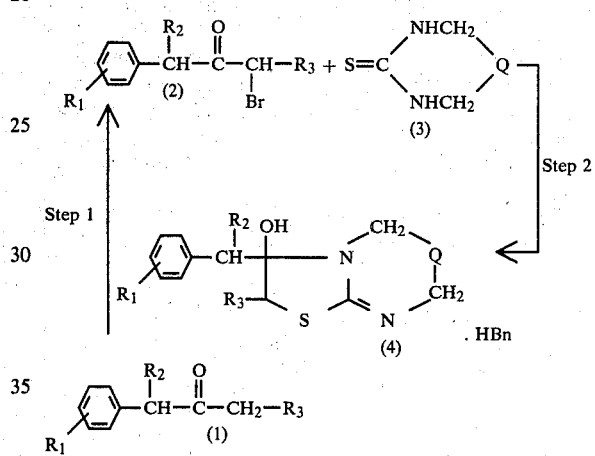

wherein $R_1$, $R_2$, $R_3$ and Q are as hereinabove defined. In accordance with this reaction scheme, a 1-aryl-2-alkanone (1) is dissolved in acetic acid and treated with about one equivalent of bromine at 60°–70° C., giving the bromo-1-aryl-2-alkanone (2). This alkanone (2) is isolated and reacted with cyclic thiourea (3) to give the product (4). If chloride is used in place of bromine, the hydrochloride salt is obtained.

In general terms, the process of step one may be carried out in acetic acid or an equivalent at 50°–80° C. for 30 minutes to 4 hours. Suitable solvents for the second step include acetone, methylethylketone, chloroform, benzene, toluene and the like and the reaction may range from 25°–60° C. for one to 72 hours. Procedures for the preparation of the 1-aryl-2-alkanones (1) are well known and may be found in such references as: M. J. Hatch and D. J. Cram, J.A.C.S., 75, 38 (1953); E. J. Cragoe, Jr., A. M. Pietruszkiewicz and C. M. Robb, J. Org. Chem., 23, 971 (1958); E. M. Schultz, U.S. Pat. No. 2,703,329. It is also possible to prepare the halo-1-aryl-2-alkanone derivatives (2) by other methods, for example, the Arndt-Eistert synthesis of an acid chloride with diazomethane and hydrobromic or hydrochloric acid [G. W. Wheland, (Advanced Organic Chemistry), John Wiley and Sons, Inc., 2nd Edition, P. 462 (1948)].

Alternatively, the compounds of Formula (4) may be prepared by treating a compound of the structure

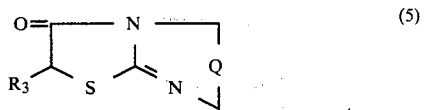

with compounds of the general structure

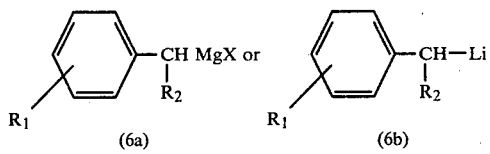

where X is a halogen other than fluorine, and $R_1$, $R_2$ and $R_3$ are as indicated above. The process is carried out by the action of a compound of the structure (6a) or (6b) upon a compound of structure (5) in an inert solvent such as diethyl ether, tetrahydrofuran, and the like, at temperatures ranging from 0° to 40° C., preferably at room temperature, for a period of 3 to 18 hours, and under an inert gas (argon or nitrogen) atmosphere. After hydrolysis of the intermediate adducts, the compounds of structure (4) are readily isolated as the free bases, which can then be converted to the desired acid addition salts.

The compounds of formula (4) can also be depicted in the equivalent tautomeric structure,

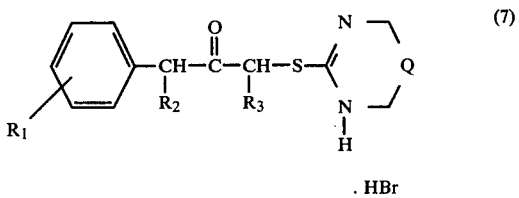

but infra-red spectral analysis of the crystalline products indicates that structure (4) is the predominant, if not the sole, configuration present. For purposes of convenience, structure (4) will be employed, but it is to be understood that all compounds of structures (4) and (7), as well as their optical isomers are in the purview of this application.

These new compounds possess diuretic activity in warm-blooded animals as established when tested by the method of P. S. Chan and D. Poorvin, Clinical and Experimental Hypertension, 1 (6), 817-830 (1979), "Sequential Method for Combined Screening Antihypertensive and Diuretic Agents in the Same Spontaneously Hypertensive Rat.". Basically this test uses male, 8 week old, spontaneously hypertensive rats of the Okamoto strain weighing about 300 g. One rat is dosed by gavage with the test compound at 100 mg./kg. of body weight with 0.9% sodium chloride loading at 25 ml./kg. of body weight at zero hour. The test compound is suspended in 2% preboiled starch at 50 mg./kg. The rat is placed in a metabolism cage and the 0-5 hour urine is collected. The urinary sodium, potassium and chloride content are determined by the Technicon Autoanalyzer; method N-20 for sodium and potassium and method N-5b for chloride. At the end of the fifth hour, the rat is placed in a regular animal cage and provided with water ad libitum. A second identical dose of the test compound is given by gavage, without sodium chloride loading, at the 24th hour. Four hours later, the rat is restrained in a supine position with elastic tapes. The femoral area is locally anesthetized by subcutaneous infiltration of 2% lidocaine. The iliac artery is isolated and punctured with a 26 gauge thin wall needle which is connected to a Statham P23Db pressure transducer-Beckman Dynograph recorder system for monitoring blood pressure. The blood pressure is recorded for 15 minutes or until it is stabilized. Based on the data obtained and using the three-stage "sequential probability ration test", statistical method, the criteria for determining if a test compound is considered active are as follows:

Test I:
If the mean arterial blood pressure (MABP) $\leq 116$ and/or the urinary sodium is $\geq 1.21$ mEq the compound is active. If the MABP is between 117–146 and/or the urinary sodium is between 1.21–0.93, a second rat is tested.

Test II:
If the average MABP of the two rats is $<122$ and/or the average urinary sodium of the two rats is $>1.16$ mEq, the compound is considered active. If the MABP is between 123–137 and/or the average urinary sodium is between 1.16–1.01, a third rat is tested.

Test III:
If the average MABP of the three rats is $\leq 128$ and/or the average urinary sodium is $\geq 1.10$, the compound is active.

The results of these tests on representative compounds of the present invention appear in Table I.

TABLE I

| Compound | Urinary Values in mEq/5 Hours | | |
|---|---|---|---|
| | Volume(ml.) | Na+ | K+ |
| 3-Diphenylmethyl-2,3,5,6,7,8-hexahydrothiazolo[3,2-a]-[1,3]diazepin-3-ol hydrobromide | 21.8 | 2.56 | 0.69 |
| 3-(p-Chloro-α-phenylbenzyl)-2,3,5,6,7,8-hexahydrothiazolo[3,2-a][1,3]diazepin-3-ol hydrobromide | 10.8 | 1.33 | 0.71 |
| 3-(p-Fluoro-α-phenylbenzyl)-2,3,5,6,7,8-hexahydrothiazolo[3,2-a][1,3]diazepin-3-ol hydrobromide | 16.0 | 2.05 | 0.76 |
| 3-(p-Bromo-α-phenylbenzyl)-2,3,5,6,7,8-hexahydrothiazolo[3,2-a][1,3]diazepin-3-ol hydrobromide | 13.8 | 1.68 | 0.62 |
| 3-[o-Chloro-α-(p-fluorophenyl)benzyl]-2,3,5,6,7,8-hexahydrothiazolo[3,2-a][1,3]diazepin-3-ol hydrobromide | 11.5 | 1.53 | 0.68 |
| 3-[o-Fluoro-α-(p-fluorophenyl)benzyl]-2,3,5,6,7,8-hexahydrothiazolo[3,2-a][1,3]diazepin-3-ol hydrobromide | 12.3 | 1.64 | 0.52 |
| 3-[m-Fluoro-α-(p-fluorophenyl)benzyl]-2,3,5,6,7,8-hexahydrothiazolo[3,2-a][1,3]diazepin-3-ol | 13.5 | 1.88 | 0.77 |

TABLE I-continued

| Compound | Urinary Values in mEq/5 Hours | | |
|---|---|---|---|
| | Volume(ml.) | Na+ | K+ |
| hydrobromide | | | |
| 3-(p-Chloro-α-phenylbenzyl)-2,3,5,6,7,8-hexahydro-2-methylthiazolo[3,2-a][1,3]diazepin-3-ol hydrobromide | 17.5 | 2.15 | 0.79 |
| 3-(p-Fluoro-α-phenylbenzyl)-2,3,5,6,7,8-hexahydro-2-methylthiazolo[3,2-a][1,3]diazepin-3-ol hydrobromide | 22.0 | 2.82 | 0.63 |
| 3-Diphenylmethyl-2,3,6,7-tetrahydro-5H-thiazolo-[3,2-a]pyrimidin-3-ol hydrobromide | 16.5 | 1.76 | 0.70 |
| 3-(p-Bromo-α-phenylbenzyl)-2,3,6,7-tetrahydro-5H-thiazolo[3,2-a]pyrimidin-3-ol hydrobromide | 11.3 | 1.41 | 0.58 |
| 3-[o-Fluoro-α-(p-fluorophenyl)benzyl]-2,3,6,7-tetrahydro-5H-thiazolo[3,2-a]pyrimidin-3-ol hydrobromide | 14.8 | 1.92 | 0.60 |
| 3-[m-Fluoro-α-(p-fluorophenyl)benzyl]-2,3,6,7-tetrahydro-5H-thiazolo[3,2-a]pyrimidin-3-ol hydrobromide | 18.0 | 2.23 | 0.62 |
| 3-[bis(p-Fluorophenyl)methyl]-2,3,6,7-tetrahydro-5H-thiazolo[3,2-a]pyrimidin-3-ol hydrobromide | 19.0 | 2.47 | 0.59 |
| 3-(p-Chloro-α-phenylbenzyl)-2,3,6,7-tetrahydro-2-methyl-5H-thiazolo[3,2-a]pyrimidin-3-ol hydrobromide | 15.0 | 1.63 | 0.91 |
| 3-(p-Fluoro-α-phenylbenzyl)-2,3,6,7-tetrahydro-2-methyl-5H-thiazolo[3,2-a]pyrimidin-3-ol hydrobromide | 16.5 | 2.04 | 0.40 |
| 3-Diphenylmethyl-2,3,6,7-tetrahydro-6,6-dimethyl-5H-thiazolo[3,2-a]pyrimidin-3-ol hydrobromide | 14.5 | 2.04 | 0.73 |
| 3-(p-Fluoro-α-phenylbenzyl)-2,3,6,7-tetrahydro-6,6-dimethyl-5H-thiazolo[3,2-a]pyrimidin-3-ol hydrobromide | 12.3 | 1.63 | 0.72 |
| 3-(p-Bromo-α-phenylbenzyl)-2,3,6,7-tetrahydro-6,6-dimethyl-5H-thiazolo[3,2-a]pyrimidin-3-ol hydrobromide | 14.3 | 1.55 | 0.72 |
| 3-[p-Chloro-α-(p-fluorophenyl)benzyl]-2,3,6,7-tetrahydro-6,6-dimethyl-5H-thiazolo[3,2-a]pyrimidin-3-ol hydrobromide | 15.0 | 1.61 | 0.99 |
| 3-[o-Chloro-α-(p-fluorophenyl)benzyl]-2,3,6,7-tetrahydro-6,6-dimethyl-5H-thiazolo[3,2-a]pyrimidin-3-ol hydrobromide | 19.3 | 2.18 | 0.80 |
| 3-[o-Fluoro-α-(p-fluorophenyl)benzyl]-2,3,6,7-tetrahydro-6,6-dimethyl-5H-thiazolo[3,2-a]pyrimidin-3-ol hydrobromide | 15.5 | 2.02 | 0.74 |
| 3-[m-Fluoro-α-(p-fluorophenyl)benzyl]-2,3,6,7-tetrahydro-6,6-dimethyl-5H-thiazolo[3,2-a]pyrimidin-3-ol hydrobromide | 15.0 | 1.77 | 0.86 |
| 3-[bis(p-Fluorophenyl)methyl]-2,3,6,7-tetrahydro-6,6-dimethyl-5H-thiazolo[3,2-a]pyrimidin-3-ol hydrobromide | 13.5 | 1.97 | 0.99 |
| 3-(p-Chloro-α-phenylbenzyl)-2,3,6,7-tetrahydro-2,6,6-trimethyl-5H-thiazolo[3,2-a]pyrimidin-3-ol hydrobromide | 11.5 | 1.40 | 0.76 |
| 3-(p-Fluoro-α-phenylbenzyl)-2,3,6,7-tetrahydro-2,6,6-trimethyl-5H-thiazolo[3,2-a]pyrimidin-3-ol hydrobromide | 16.5 | 2.04 | 0.80 |
| 3-[o-Chloro-α-(p-fluorophenyl)benzyl]-2,3,5,8-tetrahydrothiazolo[3,2-a][1,3]diazepin-3-ol hydrobromide | 11.8 | 1.37 | 0.58 |
| 3-[o-Fluoro-α-(p-fluorophenyl)benzyl]-2,3,5,8-tetrahydrothiazolo[3,2-a][1,3]diazepin-3-ol hydrobromide | 18.0 | 2.08 | 0.68 |
| 3-[m-Fluoro-α-(p-fluorophenyl)benzyl]-2,3,5,8-tetrahydrothiazolo[3,2-a][1,3]diazepin-3-ol hydrobromide | 15.5 | 1.70 | 0.60 |
| 3-Diphenylmethyl-2,3,6,7,8,9-hexahydro-5H-thiazolo-[3,2-a][1,3]diazocin-3-ol hydrobromide | 19.3 | 2.77 | 1.90 |
| 3-Benzyl-2-phenyl-2,3,6,7-tetrahydro-5H-thiazolo-[3,2-a]pyrimidin-3-ol hydrobromide | 10.8 | 1.32 | 0.48 |
| 3-Benzyl-6,6-dimethyl-2-phenyl-2,3,6,7-tetrahydro-5H-thiazolo[3,2-a]pyrimidin-3-ol hydrobromide | 15.8 | 2.14 | 0.57 |
| 3-(p-Fluorobenzyl)-2-p-fluorophenyl-2,3,5,6,7,8-hexahydrothiazolo[3,2-a][1,3]diazepin-3-ol hydrobromide | 14.0 | 1.87 | 0.62 |
| 3-(p-Fluorobenzyl)-2-p-fluorophenyl-2,3,6,7,8,9-hexahydro-5H-thiazolo[3,2-a][1,3]diazocin-3-ol hydrobromide | 20.0 | 2.10 | 0.75 |

The active compounds of the present invention are effective as diuretics in warm-blooded animals when administered in amounts ranging from about 5 mg. to about 200 mg. per kilogram of body weight per day. A preferred dosage regimen for optimum results would be from about 5 mg. to about 50 mg. per kilogram of body weight per day, and such dosage units are employed that a total of from about 350 mg. to about 3.5 g. of the active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and and 200 mg. of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The intermediate arylketones [formula (1)] are prepared essentially as described by Cragoe, et al., vide supra, as illustrated in Example 1.

EXAMPLE 1

1-(m-Fluorophenyl)-1-(p-fluorophenyl)-2-propanone

A solution of 16.5 g. or m-fluorophenyl-2-propanone [Z. Eckstein and J. Plenkiewicz, Rocznik. Chem., 37, 907 (1963)] in 70 ml. of fluorobenzene is cooled and stirred as 5.5 ml. of bromine are added dropwise. Argon gas is bubbled through the mixture for one hour. The solution is then added dropwise to a mixture of 29.6 g. of aluminum chloride and 70 ml. of fluorobenzene, stirred at 80°–90° C. Stirring is continued at this temperature for one hour then the mixture is poured into ice and 45 ml. of concentrated hydrochloric acid. Toluene is added, the organic layer is separated, washed with dilute sodium hydroxide and then water and distilled, giving the desired product as a liquid, b.p. 106°–112° C./0.15 mm.

When the appropriate 1-aryl-2-alkanone is reacted with a benzene derivative (as reagent and solvent) by the procedure described in Example 1, the intermediates Examples 2–21 (listed in tabular form) are derived.

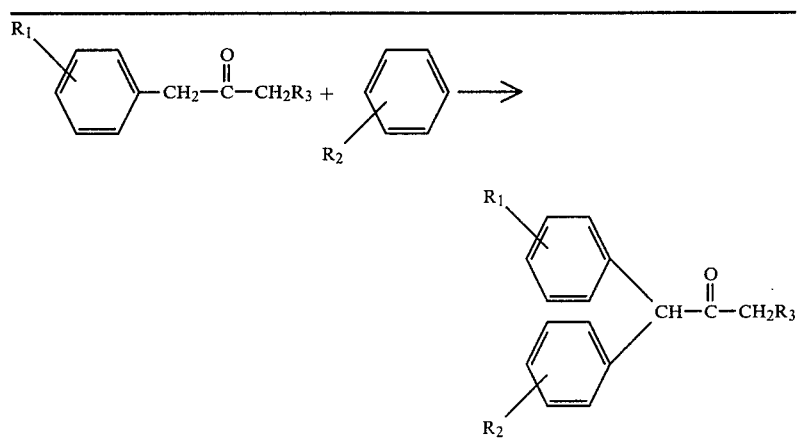

| | 1-Aryl-2-alkanone | | Benzene Derivative | | |
|---|---|---|---|---|---|
| Ex. | $R_1$ | $R_3$ | $R_2$ | Intermediate | B.P. °C./mm. |
| 2 | H | H | p-Cl | 1-(p-Chlorophenyl)-1-phenyl-2-propanone | 150–156/0.4 |

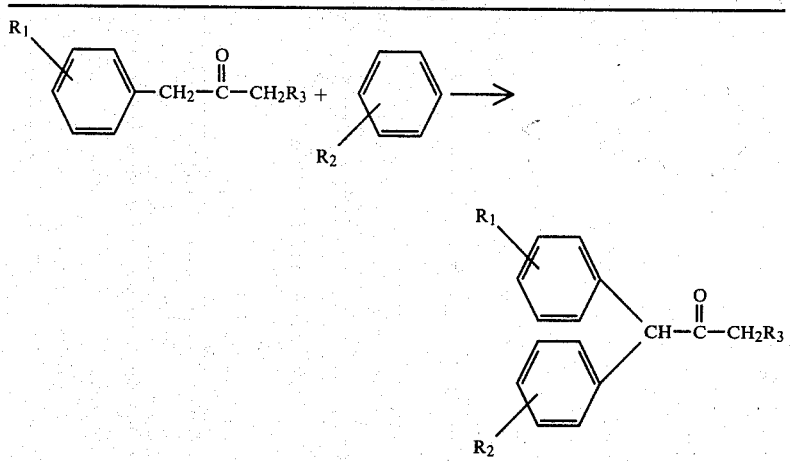

| | 1-Aryl-2-alkanone | | Benzene Derivative | | |
|---|---|---|---|---|---|
| Ex. | $R_1$ | $R_3$ | $R_2$ | Intermediate | B.P. °C./mm. |
| 3 | H | H | p-F | 1-(p-Fluorophenyl)-1-phenyl-2-propanone | 142–146/<1 |
| 4 | H | H | p-Br | 1-(p-Bromophenyl)-1-phenyl-2-propanone | 134–138/0.15 |
| 5 | H | H | p-$CH_3$ | 1-Phenyl-1-p-tolyl-2-propanone | 140–144/<1 |
| 6 | m-Cl | H | p-$CH_3$ | 1-(m-Chlorophenyl)-1-p-tolyl-2-propanone | 130–136/0.2 |
| 7 | o-F | H | p-$CH_3$ | 1-(o-Fluorophenyl)-1-p-tolyl-2-propanone | 130–136/0.2 |
| 8 | m-F | H | p-$CH_3$ | 1-(m-Fluorophenyl)-1-p-tolyl-2-propanone | 111–120/0.2 |
| 9 | p-$CH_3$ | H | p-F | 1-(p-Fluorophenyl)-1-p-tolyl-2-propanone | 116–122/0.15 |
| 10 | m-$CH_3$ | H | p-$CH_3$ | 1-m-Tolyl-1-p-tolyl-2-propanone | 126–132/0.2 |
| 11 | p-Cl | H | p-Cl | 1,1-bis(p-Chlorophenyl)-2-propanone | 170–178/<1 |
| 12 | p-Cl | H | p-F | 1-(p-Chlorophenyl)-1-(p-fluorophenyl)-2-propanone | 130–136/0.2 |
| 13 | o-Cl | H | p-F | 1-(o-Chlorophenyl)-1-(p-fluorophenyl)-2-propanone | 114–120/0.15 |
| 14 | o-F | H | p-F | 1-(o-Fluorophenyl)-1-(p-fluorophenyl)-2-propanone | 100–106/0.15 |
| 15 | m-Cl | H | p-F | 1-(m-Chlorophenyl)-1-(p-fluorophenyl)-2-propanone | 126–135/0.15 |
| 16 | p-F | H | p-F | 1,1-bis(p-Fluorophenyl)-2-propanone | 120–126/0.2 |
| 17 | m-$CH_3$ | H | p-F | 1-(p-Fluorophenyl)-1-m-tolyl-2-propanone | 116–122/0.15 |
| 18 | H | $CH_3$ | p-Cl | 1-(p-Chlorophenyl)-1-phenyl-2-butanone | 155–160/<1 |
| 19 | H | $CH_3$ | p-F | 1-(p-Fluorophenyl)-1-phenyl-2-butanone | 142–146/>1 |
| 20 | p-F | $CH_3$ | p-F | 1,1-bis(p-Fluorophenyl)-2-butanone | 128–132/0.4 |
| 21 | p-Cl | $CH_3$ | p-Cl | 1,1-bis(p-Chlorophenyl)-2-butanone | 162–168/0.2 |

EXAMPLE 22

3-Diphenylmethyl-2,3,5,6,7,8-hexahydrothiazolo[3,2-a][1,3]diazepin-3-ol hydrobromide A solution of 4.20 g. of 1,1-diphenyl-2-propanone in 25 ml. of acetic acid is heated at 60°–70° C. and 1.0 ml. of bromine in 8 ml. of acetic acid is added dropwise. The reaction mixture is held at 60°–70° C. for one hour and then poured into ice. Toluene is added. The toluene layer is separated, washed with water, dried over magnesium sulfate and concentrated to obtain 1-bromo-3,3-diphenyl-2-propanone.

The 1-bromo-3,3-diphenyl-2-propanone is dissolved in 30 ml. of acetone and added to a boiling mixture of 1.82 g. of hexahydro-2H-1,3-diazepine-2-thione in 100 ml. of acetone. This mixture is allowed to stand at room temperature for 24 hours, then the product is collected by filtration, washed with acetone and dried in vacuo at 50° C., giving the product as a solid, m.p. 194°–195° C. (dec.).

When the procedure of Example 22 is carried out using, instead of 1,1-diphenyl-2-propanone, the intermediate diarylketones of Examples 1–21, the final products of Examples 23–39 (listed in tabular form) are derived.

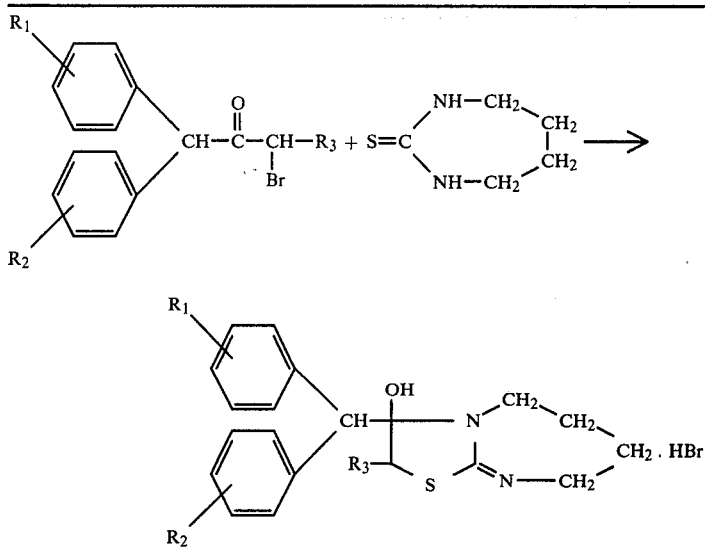

| Ex. | Intermediate Ex. No. | Product | M.P. °C. |
|---|---|---|---|
| 23 | 2 | 3-(p-Chloro-α-phenylbenzyl)-2,3,5,6,7,8-hexahydro-thiazolo[3,2-a][1,3]diazepin-3-ol hydrobromide | 202–204 |
| 24 | 3 | 3-(p-Fluoro-α-phenylbenzyl)-2,3,5,6,7,8-hexahydro-thiazolo[3,2-a][1,3]diazepin-3-ol hydrobromide | 183–185 |
| 25 | 4 | 3-(p-Bromo-α-phenylbenzyl)-2,3,5,6,7,8-hexahydro-thiazolo[3,2-a][1,3]diazepin-3-ol hydrobromide | 169–171 |
| 26 | 5 | 2,3,5,6,7,8-Hexahydro-3-(p-methyl-α-phenylbenzyl)-thiazolo[3,2-a][1,3]diazepin-3-ol hydrobromide | 198–200 |
| 27 | 7 | 3-(o-Fluoro-α-p-tolylbenzyl)-2,3,5,6,7,8-hexahydrothiazolo[3,2-a][1,3]diazepin-3-ol hydrobromide | 176–178 |
| 28 | 9 | 3-(p-Fluoro-α-p-tolylbenzyl)-2,3,5,6,7,8-hexahydrothiazolo[3,2-a][1,3]diazepin-3-ol hydrobromide | 184–186 |
| 29 | 10 | 2,3,5,6,7,8-Hexahydro-3-(m-methyl-α-p-tolylbenzyl)thiazolo[3,2-a][1,3]diazepin-3-ol hydrobromide | 191–193 |
| 30 | 12 | 3-[p-Chloro-α-(p-fluorophenyl)benzyl]-2,3,5,6,7,8-hexahydrothiazolo[3,2-a][1,3]diazepin-3-ol hydrobromide | 197–199 |
| 31 | 13 | 3-[o-Chloro-α-(p-fluorophenyl)benzyl]-2,3,5,6,7,8-hexahydrothiazolo[3,2-a][1,3]diazepin-3-ol hydrobromide | 175–177 |
| 32 | 14 | 3-[o-Fluoro-α-(p-fluorophenyl)benzyl]-2,3,5,6,7,8-hexahydrothiazolo[3,2-a][1,3]diazepin-3-ol hydrobromide | 204–206 |
| 33 | 1 | 3-[m-Fluoro-α-(p-fluorophenyl)benzyl]-2,3,5,6,7,8-hexahydrothiazolo[3,2-a][1,3]diazepin-3-ol hydrobromide | 189–191 |
| 34 | 16 | 3-[bis(p-Fluorophenyl)methyl]-2,3,5,6,7,8,hexahydrothiazolo[3,2-a][1,3]diazepin-3-ol hydrobromide | 187–189 |
| 35 | 17 | 3-(p-Fluoro-α-m-tolylbenzyl)-2,3,5,6,7,8-hexahydrothiazolo[3,2-a][1,3]diazepin-3-ol hydrobromide | 180–182 |
| 36 | 18 | 3-(p-Chloro-α-phenylbenzyl)-2,3,5,6,7,8-hexahydro-2-methylthiazolo[3,2-a]diazepin-3-ol hydrobromide | 187–189 |
| 37 | 19 | 3-(p-Fluoro-α-phenylbenzyl)-2,3,5,6,7,8-hexahydro-2-methylthiazolo[3,2][1,3]diazepin-3-ol hydrobromide | 198–200 |
| 38 | 20 | 3-[bis(p-Fluorophenyl)methyl]-2,3,5,6,7,8-hexahydro-2-methylthiazolo[3,2-a][1,3]diazepin-3-ol hydrobromide | 192–194 |
| 39 | 21 | 3-[bis(p-Chlorophenyl)methyl]-2,3,5,6,7,8-hexahydro-2-methylthiazolo[3,2-a][1,3]diazepin-3-ol hydrobromide | 197–199 |

EXAMPLE 40

3-Diphenylmethyl-2,3,5,6,7,8-hexahydrothiazolo[3,2-a][1,3]diazepin-3-ol

A solution of 4.2 g. of 3-diphenylmethyl-2,3,5,-6,7,8-hexahydrothiazolo[3,2-a][1,3]diazepin-3-ol hydrobromide in 50 ml. of 65% aqueous methanol is treated with 12 ml. of 1 N sodium hydroxide. The resulting solid is collected by filtration, washed with water and dried in vacuo at 40° C., giving the desired product, m.p. 123°–125° C.

EXAMPLE 41

3-Diphenylmethyl-2,3,5,6,7,8-hexahydrothiazolo[3,2-a][1,3]diazepin-3-ol hydrochloride A solution of 3.0 g. of 3-diphenylmethyl-2,3,5,-6,7,8-hexahydrothiazolo[3,2-a][1,3-diazepin-3-ol in 30 ml. of acetone is treated with 4 ml. of 3 N ethanolic hydrochloric acid. The resulting solid is collected by filtration, giving the desired product, m.p. 205° C. (dec.).

EXAMPLE 42

3-Diphenylmethyl-2,3,6,7-tetrahydro-5H-thiazolo-[3,2-a]pyrimidin-3-ol hydrobromide A 2.1 g. portion of 1,1-diphenyl-2-propanone is converted to 1-bromo-3,3-diphenyl-2-propanone by the procedure of Example 22. The 1-bromo-3,3-diphenyl-2-propanone is dissolved in 15 ml. of acetone and added to a boiling mixture of 0.80 g. of tetrahydro-2-pyrimidinethione in 70 ml. of acetone. This mixture is allowed to stand for 48 hours and the resulting solid is collected by filtration, giving the desired product, m.p. 196°-198° C.

When the procedure of Example 40 is carried out using, instead of 1.1-diphenyl-2-propanone, the intermediate diarylketones of Examples 1-21, the final products of Examples 43-60 (listed in tabular form) are derived.

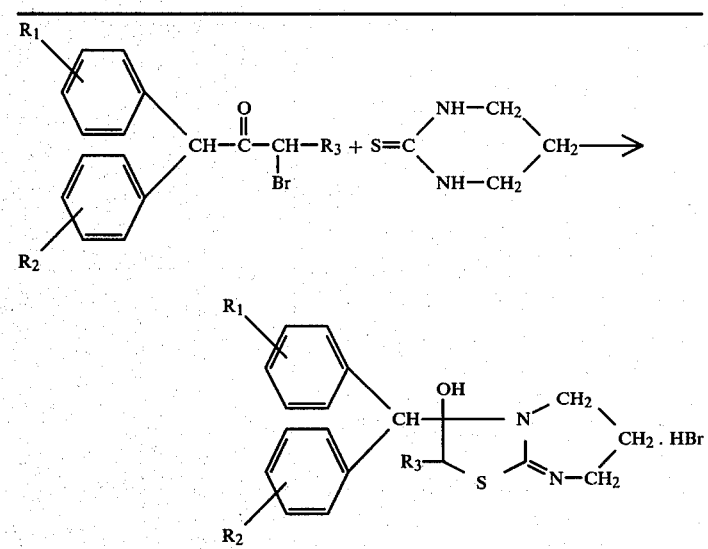

| Ex. | Intermediate Ex. No. | Product | M.P. °C. |
|---|---|---|---|
| 43 | 2 | 3-(p-Chloro-α-phenylbenzyl)-2,3,6,7-tetrahydro-5H-thiazolo[3,2-a]pyrimidin-3-ol hydrobromide | 177–179 |
| 44 | 3 | 3-(p-Fluoro-α-phenylbenzyl)-2,3,6,7-tetrahydro-5H-thiazolo[3,2-a]pyrimidin-3-ol hydrobromide | 174–176 |
| 45 | 4 | 3-(p-Bromo-α-phenylbenzyl)-2,3,6,7-tetrahydro-5H-thiazolo[3,2-a]pyrimidin-3-ol hydrobromide | 163–166 |
| 46 | 5 | 2,3,6,7-Tetrahydro-3-(p-methyl-α-phenylbenzyl)-5H-thiazolo[3,2-a]pyrimidin-3-ol hydrobromide | 163–165 |
| 47 | 6 | 3-(m-Chloro-α-p-tolylbenzyl)-2,3,6,7-tetrahydro-5H-thiazolo[3,2-a]pyrimidin-3-ol hydrobromide | 184–186 |
| 48 | 7 | 3-(o-Fluoro-α-p-tolylbenzyl)-2,3,6,7-tetrahydro-5H-thiazolo[3,2-a]pyrimidin-3-ol hydrobromide | 188–190 |
| 49 | 8 | 3-(m-Fluoro-α-p-tolylbenzyl)-2,3,6,7-tetrahydro-5H-thiazolo[3,2-a]pyrimidin-3-ol hydrobromide | 138–140 |
| 50 | 9 | 3-(p-Fluoro-α-p-tolylbenzyl)-2,3,6,7-tetrahydro-5H-thiazolo[3,2-a]pyrimid-3-ol hydrobromide | 135–137 |
| 51 | 10 | 2,3,6,7-Tetrahydro-3-(m-methyl-α-p-tolylbenzyl)-5H-thiazolo[3,2-a]pyrimidin-3-ol hydrobromide | 173–175 |
| 52 | 11 | 3-[bis(p-Chlorophenyl)methyl-2,3,6,7-tetrahydro-5H-thiazolo[3,2-a]pyrimidin-3-ol hydrobromide | 131–133 |
| 53 | 12 | 3-[p-Chloro-α-(p-fluorophenyl)benzyl]-2,3,6,7-tetrahydro-5H-thiazolo[3,2-a]pyrimidin-3-ol | 144–146 |
| 54 | 13 | 3-[o-Chloro-α-(p-fluorophenyl)benzyl]-2,3,6,7-tetrahydro-5H-thiazolo[3,2-a]pyrimidin-3-ol hydrobromide | 184–186 |
| 55 | 14 | 3-[o-Fluoro-α-(p-fluorophenyl)benzyl]-2,3,6,7-tetrahydro-5H-thiazolo[3,2-a]pyrimidin-3-ol hydrobromide | 190–192 |
| 56 | 1 | 3-[m-Fluoro-α-(p-fluorophenyl)benzyl]-2,3,6,7-tetrahydro-5H-thiazolo[3,2-a]pyrimidin-3-ol hydrobromide | 154–156 |
| 57 | 16 | 3-[bis(p-Fluorophenyl)methyl]-2,3,6,7-tetrahydro-5H-thiazolo[3,2-a]pyrimidin-3-ol hydrobromide | 172–174 |
| 58 | 18 | 3-(p-Chloro-α-phenylbenzyl)-2,3,6,7,-tertahydro-2- | 176–178 |

-continued

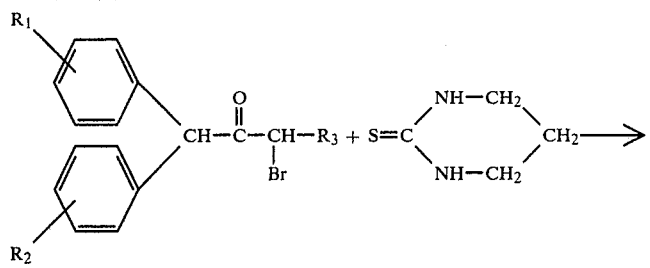

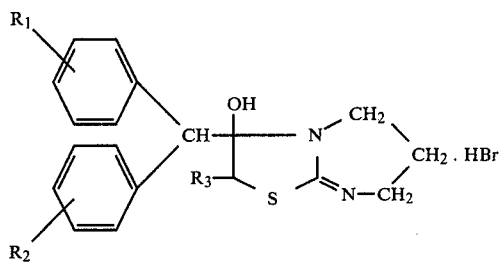

| Ex. | Intermediate Ex. No. | Product | M.P. °C. |
|---|---|---|---|
| | | methyl-5H-thiazolo[3,2-a]pyrimidin-3-ol hydrobromide | |
| 59 | 19 | 3-(p-Fluoro-α-phenylbenzyl)-2,3,6,7-tetrahydro-2-methyl-5H-thiazolo[3,2-a]pyrimidin-3-ol hydrobromide | 213–215 |
| 60 | 20 | 3-[bis(p-Fluorophenyl)methyl]-2-methyl-2,3,6,7,-tetrahydro-5H-thiazolo[3,2-a]pyrimidin-3-ol hydrobromide. | 183–5 |

EXAMPLE 61

3-Diphenylmethyl-2,3,6,7-tetrahydro-6,6-dimethyl-5H-thiazolo[3,2-a]pyrimidin-3-ol hydrobromide A 2.1 g. portion of 1,1-diphenyl-2-propanone is converted to 1-bromo-3,3-diphenyl-2-propanone as described in Example 22. This 1-bromo-3,3-diphenyl-2-propanone is dissolved in 15 ml. of acetone and added to a boiling mixture of 1.0 g. of tetrahydro-5,5-dimethyl-2(1H)-pyrimidinethione in 50 ml. of acetone. The mixture is allowed to stand at room temperature for 24 hours and the resulting solid is collected by filtration, giving the desired product, m.p. 259°–261° C.

When the procedure of Example 61 is carried out using, instead of 1,1-diphenyl-2-propanone, the intermediate diarylketones of Examples 1–21, the final products of Examples 62–78 (listed in tabular form) are derived.

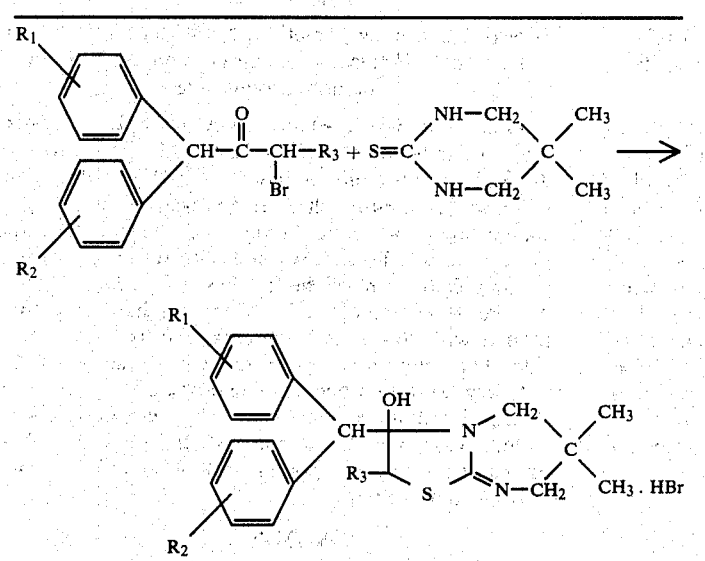

| Ex. | Intermediate Ex. No. | Product | M.P. °C. |
|---|---|---|---|
| 62 | 2 | 3-(p-Chloro-α-phenylbenzyl)-2,3,6,7-trahydro-6,6-dimethyl-5H-thiazolo[3,2-a]pyrimidin-3-ol hydrobromide | ca 180 |
| 63 | 3 | 3-(p-Fluoro-α-phenylbenzyl)-2,3,6,7-tetrahydro-6,6-dimethyl-5H-thiazolo[3,2-a]pyrimidin-3-ol hydrobromide | ca 200 |
| 64 | 4 | 3-(p-Bromo-α-phenylbenzyl)-2,3,6,7-tetrahydro-6,6-dimethyl-5H-thiazolo[3,2-a]pyrimidin-3-ol hydrobromide | 180 |
| 65 | 5 | 2,3,6,7-Tetrahydro-3-(p-methyl-α-phenylbenzyl)-6,6-dimethyl-5H-thiazolo[3,2-a]pyrimidin-3-ol hydrobromide | 169–171 |
| 66 | 6 | 3-(m-Chloro-α-p-tolybenzyl)-2,3,6,7-tetrahydro-6,6-dimethyl-5H-thiazolo[3,2-a]pyrimidin-3-ol hydrobromide | ca 200 |
| 67 | 7 | 3-(o-Fluoro-α-p-tolylbenzyl)-2,3,6,7-tetrahydro 6,6-dimethyl-5H-thiazolo[3,2-a]pyrimidin-3-ol hydrobromide | 170–172 |
| 68 | 9 | 3-(p-Fluoro-α-p-tolylbenzyl)-2,3,6,7-tetrahydro-6,6-dimethyl-5H-thiazolo[3,2-a]pyrimidin-3-ol hydrobromide | <200 |
| 69 | 12 | 3-[p-Chloro-α-(p-fluorophenyl)benzyl]-2,3,6,7-tetrahydro-6,6-dimethyl-5H-thiazolo[3,2-a]-pyrimidin-3-ol hydrobromide | 192–194 |
| 70 | 13 | 3[o-Chloro-α-(p-fluorophenyl)benyl)benzyl-2,3,6,7-tetrahydro-6,6-dimethyl-5H-thiazolo[3,2-a]-pyrimidin-3-ol hydrobromide | 205 |
| 71 | 14 | 3-[o-Fluoro-α-(p-fluorophenyl)benzyl]-2,3,6,7-tetrahydro-6,6-dimethyl-5H-thiazolo[3,2-a]-pyrimidin-3-ol hydrobromide | ca 220 |
| 72 | 1 | 3-[m-Fluoro-α-(p-fluorophenyl)benzyl]-2,3,6,7-tetrahydro-6,6-dimethyl-5H-thiazolo[3,2-a]-pyrimidin-3-ol-hydrobromide | 203 |
| 73 | 16 | 3-[bis-(p-Flourophenyl)methyl]-2,3,6,7-tetra-hydro-6,6-dimethyl-5H-thiazolo[3,2-a]pyrimidin-3-ol hydrobromide | 198–200 |
| 74 | 17 | 3-(p-Fluoro-α-m-tolylbenzyl)-2,3,6,7-tetrahydro-6,6-dimethyl-5H-thiazolo[3,2-a]pyrimidin-3-ol hydrobromide | ca 200 |
| 75 | 18 | 3-(p-Chloro-α-phenylbenzyl)-2,3,6,7-tetrahydro-trimethyl-5H-thiazolo[3,2-a]pyrimidin-3-ol hydrobromide | 166–168 |
| 76 | 19 | 3-(p-Fluoro-α-phenylbenzyl)-2,3,6,7,-tetrahydro-2,6,6-trimethyl-5H-thiazolo[3,2-a]pyrimidin-3-ol hydrobromide | 175–177 |
| 77 | 20 | 3-[bis(p-Fluorophenyl)methyl]-2,3,6,7,-tetrahydro-2,6,6,-trimethyl-5H-thiazolo[3,2-a]pyrimidin-3-ol hydrobromide | 192–3 |
| 78 | 21 | 3-[bis(p-Chlorophenyl)methyl] -2,3,6,7-tetrahydro-2,6,6,-trimethyl-5H-thiazolo[3,2,-a]pyrimidin-3-ol hydrobromide | 198–200 |

EXAMPLE 79

3-[bis(p-Fluorophenyl)methyl]-6,6-dimethyl-2,3,6,7-tetrahydro-5H-thiazolo[3,2-a]pyrimidin-3-ol and its monohydrochloride 22.8 grams of 3-[bis(p-Fluorophenyl)methyl]-6,6-dimethyl-2,3,6,7-tetrahydro-5H-thiazolo[3,2-a][1,3]-pyrimidin-3-ol hydrobromide is dissolved in 100 ml. of methanol, employing slight warming. The solution is then treated with 10 ml. of 5 N sodium hydroxide. A white precipitate soon develops. The mixture is cooled at 5° C., the precipitate collected, washed with water and dried; yield, 17.5 grams of the free base; M.P. 145°-7°. The free base is dissolved in ethanol and treated with 15 ml. of 4.4 N ethanolic hydrogen chloride. Removal of the solvent in vacuo (bath temperature 50°) leaves a white residue which after triturating with 200 ml. acetone yields 14.5 grams of the title compound, melting at 293°-295° C.

EXAMPLE 80

3-(p-Fluoro-α-phenylbenzyl)-2,3,6,7-tetrahydro-2,6,6-trimethyl-5H-thiazolo[3,2-a]pyrimidin-3-ol and its monohydrochloride 63.0 grams of 3-(p-Fluoro-α-phenylbenzyl)-2,3,6,7,-tetrahydro-2,6,6-trimethyl-5H-thiazolo[3,2-a][1,3]pyrimidin-3-ol hydrobromide is dissolved in 400 ml. of methanol, and the solution then treated with 30 ml. of 5 N sodium hydroxide, followed by 400 ml. of water. After cooling at 5° C., the precipitate is washed with water, and dried; yield of free base, 37.7 g; M.P. 138°-140° C. The free base is dissolved in 400 ml. of warm ethanol and the solution then treated with 40 ml. of 3.7 N ethanolic hydrogen chloride. Addition of 150 ml. of acetone gives a precipitate of the title compound, which after washing with acetone and drying, weighs 34.7 g. and melts at 193°-195° C., with decomposition.

EXAMPLE 81

3-[bis(p-Fluorophenyl)methyl]-2,3,6,7-tetrahydro-2,6,6-trimethyl-5H-thiazolo[3,2-a]pyrimidin-3-ol and its monohydrochloride 40 grams of 3-[bis(p-fluorophenyl)methyl]-2,3,6,7-tetrahydro-2,6,6-trimethyl-5H-thiazolo[3,2-a][1,3]pyrimidin-3-ol hydrobromide is dissolved in 150 ml. of methanol, and the solution then treated with 20 ml. of 5 N sodium hydroxide. The mixture is cooled to 5° C., the precipitate is collected, washed with water, and dried, yielding 20.0 grams of the free base; M.P. 146°-148° C. The free base is dissolved in 200 ml. of ethanol, and then treated with 20 ml. of 3.7 N ethanolic hydrogen chloride. The solution is concentrated in vacuo at 50° C., until crystallization occurs. The mixture is diluted with an equal volume of acetone. The precipitate is collected, washed with acetone and dried, yielding 15.0 grams of the title compound, melting at 184°-186° C., with decomposition.

EXAMPLE 82

3-Diphenylmethyl-2,3,5,8-tetrahydrothiazolo[3,2-a][1,3]-diazepin-3-ol hydrobromide A 4.2 g. portion of 1,1-diphenyl-2-propanone is converted to 1-bromo-3,3-diphenyl-2-propanone by the procedure of Example 22.

This 1-bromo-3,3-diphenyl-2-propanone is dissolved in 50 ml. of acetone and added to a warm solution of 1.28 g. of 1,3,4,7-tetrahydro-2H-1,3-diazepin-2-thione in 100 ml. of acetone. The reaction mixture is warmed, with stirring, for 3 hours and then stirred for 72 hours. The mixture is cooled and the resulting solid is collected by filtration, giving the desired product.

When the procedure of Example 82 is carried out using, instead of 1,1-diphenyl-2-propanone, the intermediate diarylketones of Examples 1-21, the final products of Examples 83-91 (listed in tabular form) are derived.

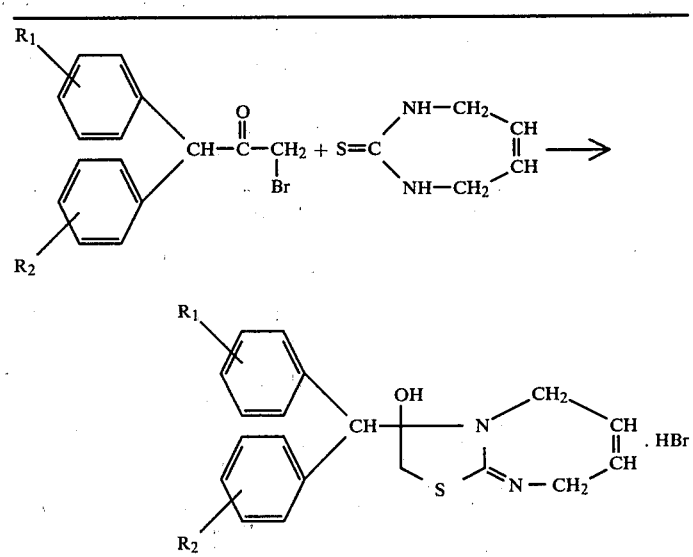

| Ex. | Intermediate Ex. No. | Product | M.P. °C. |
|---|---|---|---|
| 83 | 2 | 3-(p-Chloro-α-phenylbenzyl)-2,3,5,8-tetrahydro-thiazolo[3,2-a][1,3]diazepin-3-ol hydrobromide | 183-185 |
| 84 | 5 | 2,3,5,8-Tetrahydro-3-(p-methyl-α-phenylbenzyl)- | 177-179 |

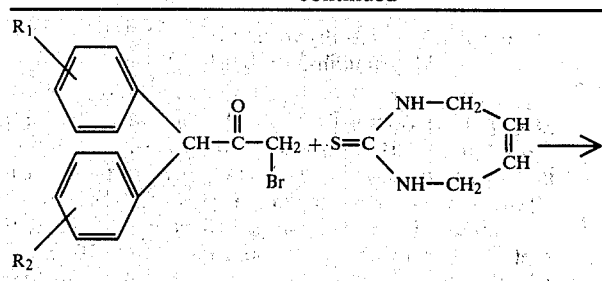

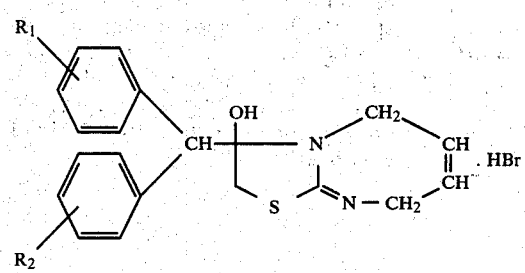

| Ex. | Intermediate Ex. No. | Product | M.P. °C. |
|---|---|---|---|
|  |  | thiazolo[3,2-a][1,3]diazepin-3-ol hydrobromide |  |
| 85 | 6 | 3-(m-Chloro-α-p-tolylbenzyl)-2,3,5,8-tetrahydro-thiazolo[3,2-a][1,3]diazepin-3-ol hydrobromide | 168–171 |
| 86 | 8 | 3-(m-Fluoro-α-p-tolylbenzyl)-2,3,5,8-tetrahydro-thiazolo[3,2-a][1,3]diazepin-3-ol hydrobromide | 155–165 |
| 87 | 17 | 3-(p-Fluoro-α-m-tolylbenzyl)-2,3,5,8-tetrahydro-thiazolo[3,2-a][1,3]diazepin-3-ol hydrobromide | 181–183 |
| 88 | 13 | 3-[o-Chloro-α-(p-fluorophenyl)benzyl]-2,3,5,8-tetrahydrothiazolo[3,2-a][1,3]diazepin-3-ol hydrobromide | 204–206 |
| 89 | 14 | 3-[o-Fluoro-α-(p-fluorophenyl)benzyl]-2,3,5,8-tetrahydrothiazolo[3,2-a][1,3]diazepin-3-ol hydrobromide | 210–212 |
| 90 | 1 | 3-[m-Fluoro-α-(p-fluorophenyl)benzyl]-2,3,5,8-tetrahydrothiazolo[3,2-a][1,3]diazepin-3-ol hydrobromide | 176–178 |
| 91 | 16 | 3-[bis(p-Fluorophenyl)methyl]-2,3,5,8-tetrahydro-thiazolo[3,2-a][1,3]diazepin-3-ol hydrobromide | 174–176 |

EXAMPLE 92

3-Diphenylmethyl-2,3,6,7,8,9-hexahydro-5H-thiazolo[3,2-a][1,3]diazocin-3-ol hydrobromide 1-Bromo-3,3-diphenyl-2-propanone is reacted with hexahydro-1,3-diazocin-2(1H)-thione by the procedure of Example 22, giving the desired product, m.p. 211°–213° C. (dec.).

EXAMPLE 93

1-Bromo-1,3-diphenyl-2-propanone

The synthesis of the requisite 1,3-diaryl-2-propanones is readily accomplished by a variety of synthetic procedures (see "Synthetic Organic Chemistry", R. B. Wagner and H. D. Zook, John Wiley and Sons [publisher], New York, N.Y., 1953). They are also conveniently obtained as a high boiling residue in the preparation of 1-aryl-2-propanones

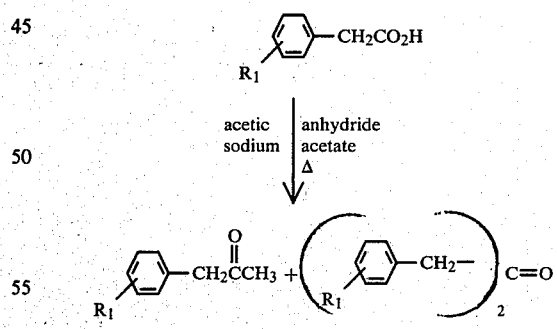

A solution of 8.4 grams of 1,3-diphenyl-2-propanone in 80 ml. of methylene chloride is stirred as a solution of 1.5 ml. of bromine in 30 ml. of methylene chloride is added dropwise. The loss of bromine coloration in the reaction solution is very rapid. The methylene chloride is then removed in vacuo (bath temperature 40° C.), and the residual 1-bromo-1,3-diphenyl-2-propanone is utilized directly in subsequent chemical reactions.

Additional 1,3-diaryl-2-propanones (Examples 94–99), prepared by the procedure cited in Example 93, are listed in tabular form. They are converted to their bromo derivatives by the same procedure as described in Example 93.

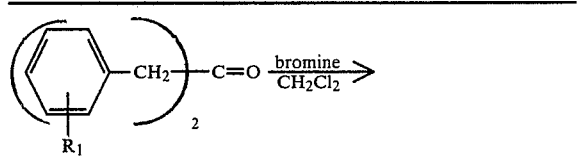

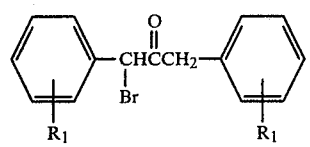

| Example | 1,3-Diaryl-2-propanone $R_1$ | M.P. or B.P. |
|---|---|---|
| 94 | m-F | b.p. 128°–132° C. (0.2mm.) |
| 95 | p-F | m.p. 62°–4° C. |
| 96 | p-Cl | m.p. 97°–99° C. |
| 97 | p-Br | M.P. 118°–120° C. |
| 98 | m-CH$_3$ | b.p. 130°–134° C. (0.15mm.) |
| 99 | p-CH$_3$ | m.p. 53°–55° C. |

EXAMPLE 100

3-Benzyl-2,3,6,7-tetrahydro-2-phenyl-5H-thiazolo[3,2-a]pyrimidin-3-ol hydrobromide A solution of 2.9 grams of 1-bromo-1,3-diphenyl-2-propanone (Example 93) in 30 ml. of acetone is added to a solution of 1.16 grams of tetrahydro-2-pyrimidinethione in 100 ml. of acetone. A white precipitate forms in a few minutes. After standing at room temperature for four hours, the precipitate is collected, washed with acetone, and dried. Recrystallization from 20 ml. of ethanol yields 2.3 grams of the pure compound, melting at 192°–194° C. with decomposition.

When the procedures of Examples 93 and 100 are applied, utilizing the 1,3-diaryl-2-propanones of Examples 93–99, and the listed cyclic thioureas, the final products of Examples 101–117 (listed in tabular form) are obtained.

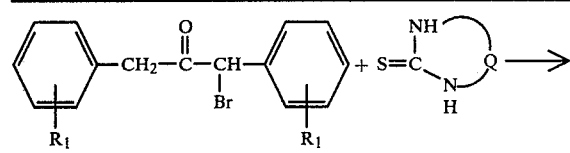

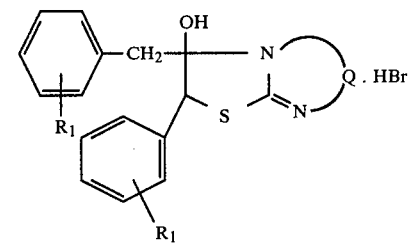

| Ex. | Intermediate Ex. No. | Q | Product | M.P. °C. |
|---|---|---|---|---|
| 101 | 95 | —(CH$_2$)$_3$— | 3-(p-Fluorobenzyl-2-(p-fluorophenyl-2,3,6,7-tetrahydro-5H-thiazolo[3,2-a]pyrimidin-3-ol hydrobromide | 193–195 |
| 102 | 98 | —CH$_2$—C(CH$_3$)$_2$—CH$_2$— | 6,6-Dimethyl-3-(m-methylbenzyl-2,3,6,7-tetrahydro-2-m-tolyl-5H-thiazolo[3,2-a]pyrimidin-3-ol hydrobromide | 185–187 |
| 103 | 97 | —CH$_2$—C(CH$_3$)$_2$—CH$_2$— | 3-p-bromobenzyl-2-p-bromophenyl-6,6-dimethyl-2,3,6,7-tetrahydro-5H-thiazolo[3,2-a]pyrimidin-3-ol hydrobromide | 186–187 |
| 104 | 99 | —CH$_2$—C(CH$_3$)$_2$—CH$_2$— | 6,6-dimethyl-3-(p-methylbenzyl)-2,3,6,7-tetrahydro-2-p-tolyl-5H-thiazolo[3,2-a]pyrimidin-3-ol hydrobromide | 163–165 |
| 105 | 93 | —CH$_2$—C(CH$_3$)$_2$—CH$_2$— | 3-benzyl-6,6-dimethyl-2-phenyl-2,3,6,7-tetrahydro-5H-thiazolo[3,2-a]pyrimidin-3-ol hydrobromide | 153–155 |

-continued

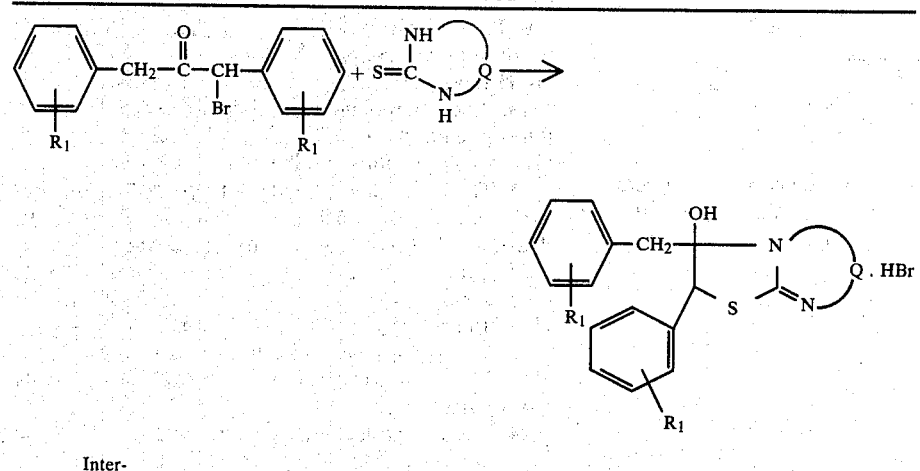

| Ex. | Intermediate Ex. No. | Q | Product | M.P. °C. |
|---|---|---|---|---|
| 106 | 95 | —CH$_2$—C(CH$_3$)$_2$—CH$_2$— | 6,6-dimethyl-3-(p-fluorobenzyl)-2-p-fluorophenyl-2,3,6,7-tetrahydro-5H-thiazolo[3,2-a]pyrimidin-3-ol hydrobromide | 181–183 |
| 107 | 93 | —(CH$_2$)$_4$— | 3-benzyl-2,3,5,6,7,8-hexahydro-2-phenylthiazolo-[3,2-a][1,3]diazepin-3-ol hydrobromide | 165–167 |
| 108 | 95 | —(CH$_2$)$_4$— | 3-p-fluorobenzyl-2-p-fluorophenyl-2,3,5,6,7,8-hexahydrothiazolo[3,2-a][1,3]diazepin-3-ol hydrobromide | 166–168 |
| 109 | 99 | —(CH$_2$)$_4$— | 2,3,5,6,7,8-Hexahydro-3-m-methylbenzyl-2-m-tolyl-thiazolo[3,2-a][1,3]diazepin-3-ol hydrobromide | 184–186 |
| 110 | 94 | —(CH$_2$)$_4$— | 3-m-fluorobenzyl-2-m-fluorophenyl-2,3,5,6,7,8-hexahydrothiazolo[3,2-a][1,3]diazepin-3-ol hydrobromide | 178–180 |
| 111 | 95 | —CH$_2$CH=CH—CH$_2$— | 3-p-fluorobenzyl-2-p-fluorophenyl-2,3,5,8-tetrahydrothiazolo[3,2-a][1,3]diazepin-3-ol hydrobromide | |
| 112 | 93 | —(CH$_2$)$_5$— | 3-benzyl-2,3,6,7,8,9-hexahydro-2-phenyl-5H-thiazolo[3,2-a][1,3]diazocin-3-ol hydrobromide | 193–195 |
| 113 | 95 | —(CH$_2$)$_5$— | 3-p-fluorobenzyl-2-p-fluorophenyl-2,3,6,7,8,9-hexahydro-5H-thiazolo[3,2-a][1,3]diazocin-3-ol hydrobromide | 205–207 |
| 114 | 94 | —(CH$_2$)$_5$— | 3-m-fluorobenzyl-2-m-fluorophenyl-2,3,6,7,8,9-hexahydro-5H-thiazolo[3,2-a][1,3]diazocin-3-ol hydrobromide | 189–191 |
| 115 | 96 | —(CH$_2$)$_5$— | 3-p-chlorobenzyl-2-p-chlorophenyl-2,3,6,7,8,9-hexahydro-5H-thiazolo[3,2-a][1,3]diazocin-3-ol hydrobromide | 206–208 |
| 116 | 99 | —(CH$_2$)$_5$— | 2,3,6,7,8,9-hexahydro-3-p-methylbenzyl-2-p-tolyl-5H-thiazolo[3,2-a][1,3]diazocin-3-ol hydrobromide | 168–170 |
| 117 | 97 | —(CH$_2$)$_5$— | 3-p-bromobenzyl-2-p-bromophenyl-2,3,6,7,8,9-hexahydro-5H-thiazolo[3,2-a][1,3]diazocin-3-ol hydrobromide | 212–214 |

EXAMPLE 118

3-Benzyl-6,6-dimethyl-2-phenyl-2,3,6,7-tetrahydro-5H-thiazolo[3,2-a]pyrimidin-3-ol Sixty five and seven-tenths grams of 2-benzyl-6,6-dimethyl-3-phenyl-2,3,6,7-tetrahydro-5H-thiazolo[3,2-a][1,3]pyrimidin-3-ol hydrobromide (Example 94A) is dissolved in 400 ml. of methanol and the solution then treated, successively, with 35 ml. of 5 normal sodium hydroxide solution and 400 ml. of water. Concentration of the solution in vacuo to remove the methanol yields a suspension of the title compound in water. The precipitate is collected, washed with water and dried. The yield is 56.0 grams and the product melts at 150°–152° C.

EXAMPLE 119

3-Benzyl-6,6-dimethyl-2-phenyl-2,3,6,7-tetrahydro-5H-thiazolo]3,2-a]pyrimidin-3-ol hydrochloride Fifty three grams of 3-benzyl-6,6-dimethyl-2-phenyl-2,3,6,7-tetrahydro-5H-thiazolo[3,2-a][1,3]pyrimidin-3-ol and 400 ml. of acetone are combined and stirred vigorously as 160 ml. of 1.1 N hydrogen chloride solution in ethanol is added during a five minute period. The mixture is then stirred another two hours, the precipitate collected, washed with acetone and dried. There is obtained 44.6 grams of the title compound, melting at 160°–162° C. with decomposition.

We claim:

1. A compound selected from those of the formula:

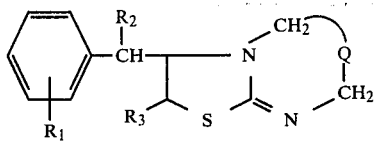

wherein $R_1$ is hydrogen, fluoro, chloro, bromo, alkyl having from 1 to 3 carbon atoms or alkoxy having from 1 to 3 carbon atoms; $R_2$ is hydrogen or

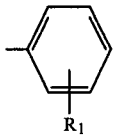

wherein $R_1$ is as hereinbefore defined; $R_3$ is hydrogen, alkyl having from 1 to 3 carbon atoms, or a moiety selected from the group consisting of those of the formulae:

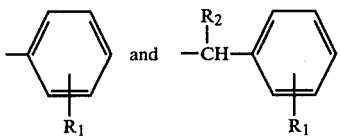

wherein $R_1$ and $R_2$ are as hereinbefore defined, and Q is a divalent moiety selected from the group consisting of those of the formulae:

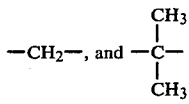

as well as the pharmaceutically acceptable salts thereof.

2. The compound according to claim 1, 3-diphenyl-methyl-2,3,6,7-tetrahydro-5H-thiazolo[3,2-a]pyrimidin-3-ol hydrobromide.

3. The compound according to claim 1, 3-[m-fluoro-α-(p-fluorophenyl)benzyl]-2,3,6,7-tetrahydro-5H-thiazolo[3,2-a]pyrimidin-3-ol hydrobromide.

4. The compound according to claim 1, 3-[bis(p-fluorophenyl)methyl]-2,3,6,7-tetrahydro-5H-thiazolo[3,2-a]pyrimidin-3-ol hydrobromide.

5. The compound according to claim 1, 3-(p-fluoro-α-phenylbenzyl)-2,3,6,7-tetrahydro-2-methyl-5H-thiazolo[3,2-a]pyrimidin-3-ol hydrobromide.

6. The compound according to claim 1, 3-diphenyl-methyl-2,3,6,7-tetrahydro-6,6-dimethyl-5H-thiazolo[3,2-a]-pyrimidin-3-ol hydrobromide.

7. The compound according to claim 1, 3-(p-fluoro-α-phenylbenzyl)-2,3,6,7-tetrahydro-6,6-dimethyl-5H-thiazolo[3,2-a]pyrimidin-3-ol hydrobromide.

8. The compound according to claim 1, 3-[o-chloro-α-(p-fluorophenyl)benzyl]-2,3,6,7-tetrahydro-6,6-dimethyl-5H-thiazolo[3,2-a]pyrimidin-3-ol hydrobromide.

9. The compound according to claim 1, 3-[o-fluoro-α-(p-fluorophenyl)benzyl]-2,3,6,7,-tetrahydro-6,6-dimethyl-5H-thiazolo[3,2-a]pyrimidin-3-ol hydrobromide.

10. The compound according to claim 1, 3-[bis(p-fluorophenyl)methyl]-2,3,6,7-tetrahydro-6,6-dimethyl-5H-thiazolo[3,2-a]pyrimidin-3-ol hydrobromide.

11. The compound according to claim 1, 3-(p-fluoro-α-phenylbenzyl)-2,3,6,7-tetrahydro-2,6,6-trimethyl-5H-thiazolo[3,2-a]pyrimidin-3-ol hydrochloride.

12. The compound according to claim 1, 3-[bis(p-fluorophenyl)methyl]-2,3,6,7-tetrahydro-2,6,6-trimethyl-5H-thiazolo[3,2-a]pyrimidin-3-ol hydrochloride.

13. The compound according to claim 1, 3-benzyl-2-phenyl-2,3,6,7-tetrahydro-5H-thiazolo[3,2-a]pyrimidin-3-ol hydrobromide.

14. The compound according to claim 1, 3-[p-chloro-α-(p-fluorophenyl)benzyl]-2,3,6,7-tetrahydro-5H-thiazolo[3,2-a]pyrimidin-3-ol hydrobromide.

15. The compound according to claim 1, 3-[p-chloro-α-phenyl)benzyl]-2-methyl-2,3,6,7-tetrahydro-5H-thiazolo[3,2-a]pyrimidin-3-ol hydrobromide.

16. The compound according to claim 1, 3-(p-chloro-α-phenyl)benzyl-2,3,6,7-tetrahydro-5H-thiazolo[3,2-a]pyrimidin-3-ol hydrobromide.

17. A compound according to claim 1, 3-[o-fluoro-α-(p-fluorophenyl)benzyl]-2,3,6,7-tetrahydro-5H-thiazolo[3,2-a]pyrimidin-3-ol hydrobromide.

18. A compound according to claim 1, 3-[p-bromo-α-phenyl)benzyl]-2,3,6,7,tetrahydro-5H-thiazolo[3,2-a]pyrimidin-3-ol hydrobromide.

19. A compound according to claim 1, 3-(p-fluoro-α-phenyl)benzyl-2-methyl-2,3,6,7-tetrahydro-5H-thiazolo[3,2-a]pyrimidin-3-ol hydrobromide.

20. A compound according to claim 1, 3-[o-chloro-α-(p-fluorophenyl)benzyl]-2,3,6,7-tetrahydro-5H-thiazolo[3,2-a]pyrimidin-3-ol hydrobromide.

21. A compound according to claim 1, 3-[bis(p-fluorophenyl)methyl]-2-methyl-2,3,6,7-tetrahydro-5H-thiazolo[3,2-a]pyrimidin-3-ol hydrobromide.

22. A compound according to claim 1, 3-(p-chloro-α-phenyl)benzyl-6,6-dimethyl-2,3,6,7-tetrahydro-thiazolo[3,2-a]pyrimidin-3-ol hydrobromide.

23. A compound according to claim 1, 3-[m-fluoro-α-(p-fluorophenyl)benzyl]-6,6-dimethyl-2,3,6,7-tetrahydro-5H-thiazolo[3,2-a]pyrimidin-3-ol hydrobromide.

24. A compound according to claim 1, 3-(p-chloro-α-phenyl)benzyl-2,3,6,7-tetrahydro-2,6,6-trimethyl-5H-thiazolo[3,2-a]pyrimidin-3-ol hydrobromide.

25. A compound according to claim 1, 3-(p-bromo-α-phenyl)benzyl-6,6-dimethyl-2,3,6,7-tetrahydro-5H-thiazolo[3,2-a]pyrimidin-3-ol hydrobromide.

26. A compound according to claim 1, 3-[p-fluoro-α-(m-tolyl)benzyl]-6,6-dimethyl-2,3,6,7-tetrahydro-5H-thiazolo[3,2-a]pyrimidin-3-ol hydrobromide.

27. A compound according to claim 1, 3-benzyl-6,6-dimethyl-2-phenyl-2,3,6,7-tetrahydro-5H-thiazolo[3,2-a]pyrimidin-3-ol hydrobromide.

* * * * *